(12) United States Patent
Bergman et al.

(10) Patent No.: US 8,978,997 B2
(45) Date of Patent: Mar. 17, 2015

(54) AROMATIC COVER

(75) Inventors: Jeffrey Bergman, Cave Creek, AZ (US); Yao Lujian, Shanghai (CN)

(73) Assignee: Fabrictech 2000, LLC, Fairfield, NJ (US)

( * ) Notice: Subject to any disclaimer, the term of this patent is extended or adjusted under 35 U.S.C. 154(b) by 587 days.

(21) Appl. No.: 13/371,917

(22) Filed: Feb. 13, 2012

(65) Prior Publication Data

US 2013/0206860 A1   Aug. 15, 2013

(51) Int. Cl.
A24F 25/00 (2006.01)
A47G 9/00 (2006.01)
A61L 9/12 (2006.01)

(52) U.S. Cl.
CPC .. *A47G 9/007* (2013.01); *A61L 9/12* (2013.01)
USPC .......................................................... 239/36

(58) Field of Classification Search
CPC ................................. A47G 9/007; A61L 9/12
USPC .......................................... 239/36, 53–56, 57
See application file for complete search history.

(56) References Cited

U.S. PATENT DOCUMENTS

| 5,299,335 A | 4/1994 | Ivester et al. |
| 5,899,785 A * | 5/1999 | Groten et al. ................. 442/334 |
| 5,918,333 A * | 7/1999 | Takashima ........................ 5/641 |
| 2002/0095726 A1 | 7/2002 | Michetti |
| 2008/0028520 A1 | 2/2008 | Rosier |

FOREIGN PATENT DOCUMENTS

| DE | 20 2010 015756 | 2/2011 |
| DE | 20 2011 050740 | 12/2011 |

OTHER PUBLICATIONS

PCT International Search Report corresponding to PCT Application PCT/US2013/020823, filed Jan. 9, 2013, International Search Report issued Mar. 21, 2013, pp. 1-5.
PCT Written Opinion of the International Search Authority corresponding to PCT Application No. PCT/US2013/020823, Written Opinion issued Mar. 21, 2013, pp. 6-9.

* cited by examiner

*Primary Examiner* — Christopher Kim
(74) *Attorney, Agent, or Firm* — Renner, Otto, Boisselle & Sklar, LLP

(57) ABSTRACT

An aromatic cover is provided. An aromatic cover includes a flexible enclosure defining an outer surface and an inner surface. A cartridge fastener is attached to the inner surface. The cartridge fastener is configured to releasably retain an aromatic cartridge containing a quantity of aromatic material at a semi-fixed position along the inner surface. An aroma-permeable region of the flexible enclosure is proximate to the semi-fixed position, wherein the aroma-permeable region is configured to allow for a release of the aromatic material from the aromatic cartridge to the outer surface.

12 Claims, 5 Drawing Sheets

AROMATIC COVER

TECHNICAL FIELD

This invention relates generally to an aromatic cover, and more particularly to an aromatic cover for use as bed linen, such as a mattress or pillow protector.

BACKGROUND

Certain aromatic materials are known to induce sleep and have been incorporated into bed linens, including mattress and pillow protectors, for such purposes. However, regular aromatic bed linens usually do not allow for control over the placement and release of aromatic materials. For example, aromatic pillows generally do not allow for aromatic materials to be directed to a particular area of the body for maximized comfort.

While providing a larger quantity of aromatic materials or lining an entire bed linen with aromatic materials may ultimately deliver more aromatic material to a user, there is always a possibility that such an untargeted solution can cause discomfort for certain users. In some cases, the unpleasantness may cause some users to avoid aromatic bed linens altogether. Further, unprotected aromatic materials may introduce dust mites, mold (via moisture infiltration) and other allergens to bed linens that, unless controlled, can make certain aromatic bed linens harmful to a user.

SUMMARY

In an embodiment, a moisture and dust mite-resistant cover comprises a flexible enclosure defining an outer surface and an inner surface. A cartridge fastener is attached to the inner surface. The cartridge fastener is configured to releasably retain an aromatic cartridge at a semi-fixed position along the inner surface. An aroma-permeable region of the flexible enclosure is proximate to the semi-fixed position. An aromatic cartridge may be attached via the cartridge fastener at the semi-fixed location. The aromatic cartridge may comprise a quantity of aromatic material, and an aroma-permeable surface enclosing the aromatic material. The aromatic material may be controllably released via the aroma-permeable surface. The aroma-permeable region may be substantially equal in size and shape to the aromatic cartridge. The cartridge fastener may be one of a button, zipper, tie-string, or hook-and-loop (e.g., Velcro®) type fastener.

In accordance with an embodiment, the aromatic material may be infused with one of a lavender dry bud, potpourri, rose, sagebrush or chamomile aroma.

In accordance with an embodiment, the flexible enclosure further comprises an open end and a closure means for closing the open end. The closure means may be one of a button, zipper, tie-string, or hook-and-loop (e.g., Velcro®) type fastener.

In accordance with an embodiment, the flexible enclosure may be fabric and multi-sided, while the aroma-permeable region may be made of a microfilament (e.g., Evolon®) material. An intersection of at least two sides of the flexible enclosure may define an outer edge, and the aroma-permeable region may be directed along an outer edge of the flexible enclosure. The flexible enclosure may be sized and shaped to at least partially enclose one of a pillow or mattress.

These and other advantages of the present disclosure will be apparent to those of ordinary skill in the art by reference to the following detailed description and the accompanying drawings.

DETAILED DESCRIPTION

FIGS. 1-6 illustrate an aromatic cover in accordance with embodiments herein. The aromatic cover of the various embodiments allows for control over the placement and release of aromatic materials, including allowing for aromatic materials to be directed to a particular area of the body for maximized comfort in bed linens, such as mattress and pillow protectors. Further, the aromatic cover of the various embodiments includes protection against dust mites, mold (via moisture infiltration) and other allergens that can otherwise make bed linens harmful to a user. It should be noted that while the term linen as used herein may include bedding sheets, covers, spreads, etc. made of linen fabric, linen is also used herein as a general term for bedding sheets, covers, spreads, etc. which may incorporate, or be made wholly out of, other materials such as cotton, polyester knit, polyurethane (plastic), wool, cashmere or the like.

Figure 1A:
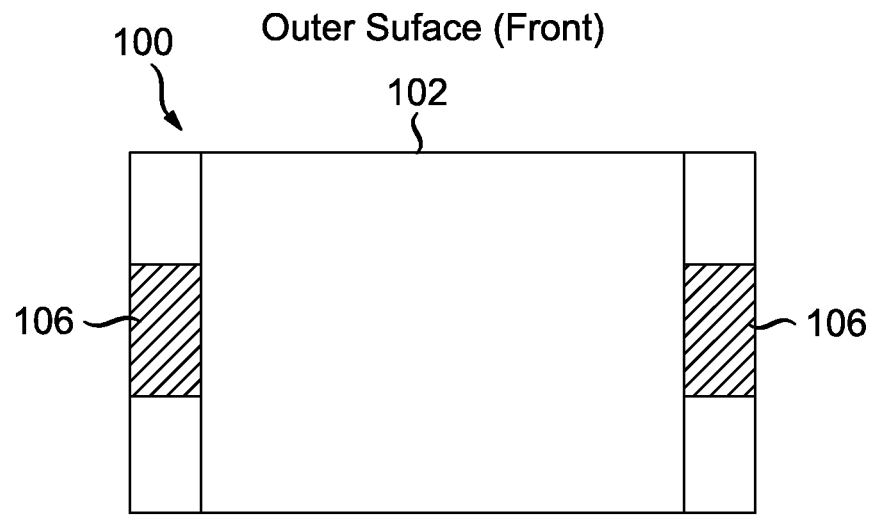
FIG. 1A is a front view of an outer surface of an aromatic cover in accordance with an embodiment.

FIG. 1A is a front view of an outer surface of an aromatic cover in accordance with an embodiment. An aromatic cover 100 includes a flexible enclosure 102. Flexible enclosure 102 defines an outer surface 104 and an inner surface, which is further described below. In one embodiment, flexible enclosure 102 may be substantially made of any flexible material, including fabrics such as cotton, polyester knit, linen, wool, cashmere or the like.

Flexible enclosure 102 further includes one or more aroma-permeable regions 106. In one embodiment, aroma-permeable regions 106 may be positioned at various locations along flexible enclosure 102. In particular, aroma-permeable regions 106 may be positioned based on how aromatic cover 100 may be typically used. For example, aroma-permeable regions 106 may be positioned at head, foot and side locations relative to a typical user.

An aroma-permeable region 106 includes a porous material for releasing aromatic material from an inner surface of flexible closure 102 to outer surface 104. For example, the porous material of aroma-permeable region 106 may be a microfilament (e.g., Evolon®) material that is different from the material of the remainder of outer surface 104.

Figure 1B:
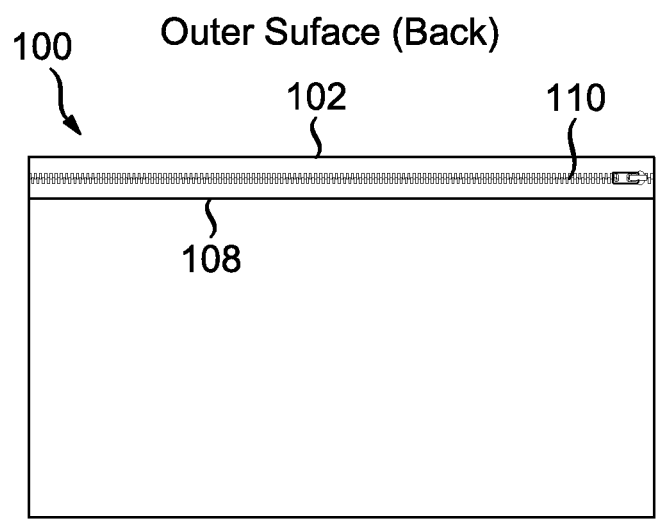
FIG. 1B is a back view of an outer surface of an aromatic cover in accordance with an embodiment.

Flexible enclosure 102 may also include an open end 108, as shown in FIG. 1B. Open end 108 may be included for receiving, and at least partially enclosing within flexible enclosure 102, a pillow, mattress or the like. For example, flexible enclosure 102 may include a fastener 110 for releasably closing open end 108, such as a button, zipper, tie string, or hook-and-loop type fastener.

Figure 2:
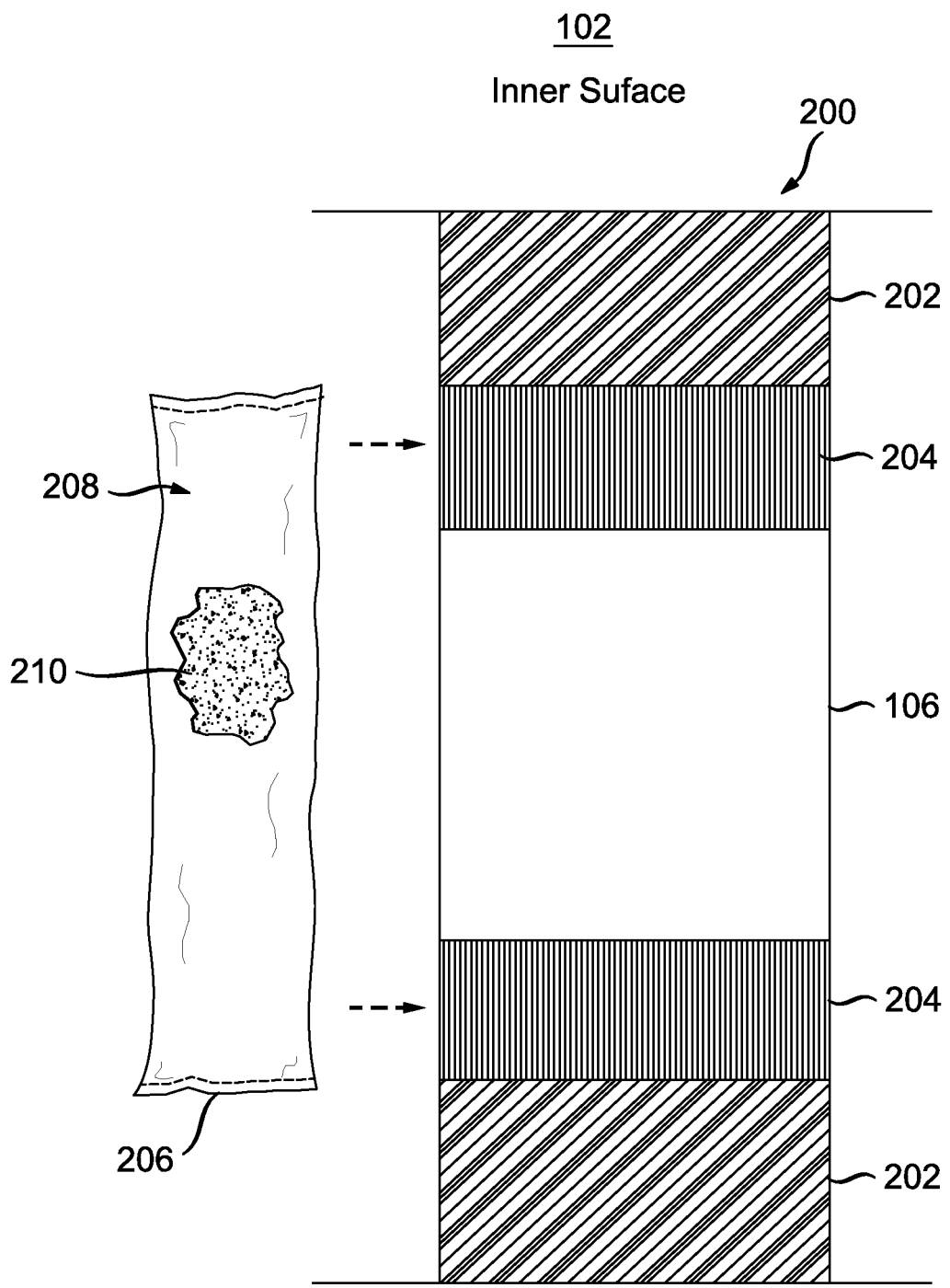
FIG. 2 is a plan view of an inner surface of an aromatic cover in accordance with an embodiment.

FIG. 2 is a plan view of an inner surface of an aromatic cover in accordance with an embodiment. The inner surface 200 of flexible enclosure 102 includes aroma-permeable region 106, a laminated fabric portion 202 and one or more cartridge fasteners 204. In one embodiment, laminated fabric portion 202 reinforces flexible enclosure 102 in areas proximate to aroma-permeable region 106. For example, laminated fabric portion 202 may prevent aroma-permeable region 106 from comprising the structural integrity of flexible enclosure 102. As such, laminated fabric portion 202 may frame one or more edges of aroma-permeable region 106 as shown or, alternatively, extend along the entire length of aroma-permeable region 106.

The one or more cartridge fasteners 204 are configured to receive a cartridge 206. Cartridge 206 comprises an aroma-permeable shell 208 that encloses and secures a quantity of aromatic material 210. For example, aromatic material 210 may be a material infused with an aroma that is generally known to induce sleep or relaxation such as lavender dry bud, potpourri, rose or sagebrush.

In one embodiment, aroma-permeable shell 208 of cartridge 206 is substantially made of a fabric material (e.g., a brushed polyester knit material), such that cartridge 206 may be received by cartridge fasteners 204. For example, cartridge fasteners 204 may be hook-and-loop type fasteners (e.g., one or more Velcro® strips) for releasably retaining cartridge 206 at a semi-fixed position along inner surface 200. Alternatively, cartridge fasteners 204 may be button, zipper, or tie-string type fasteners.

In one embodiment, cartridge 206 may be received by cartridge fasteners 204 such that aroma-permeable region 106 is proximate to a semi-fixed position of cartridge 206. For example, aroma-permeable region 106 may be substantially equal in size and shape to cartridge 206, thereby contributing to a controlled release of aromatic material 210 from inner surface 200 to outer surface 104 via aroma-permeable region 106. Alternatively, aroma-permeable region 106 may be positioned, sized or shaped to direct a controlled release of aromatic material 210 to specified locations along outer surface 104.

Figure 3:
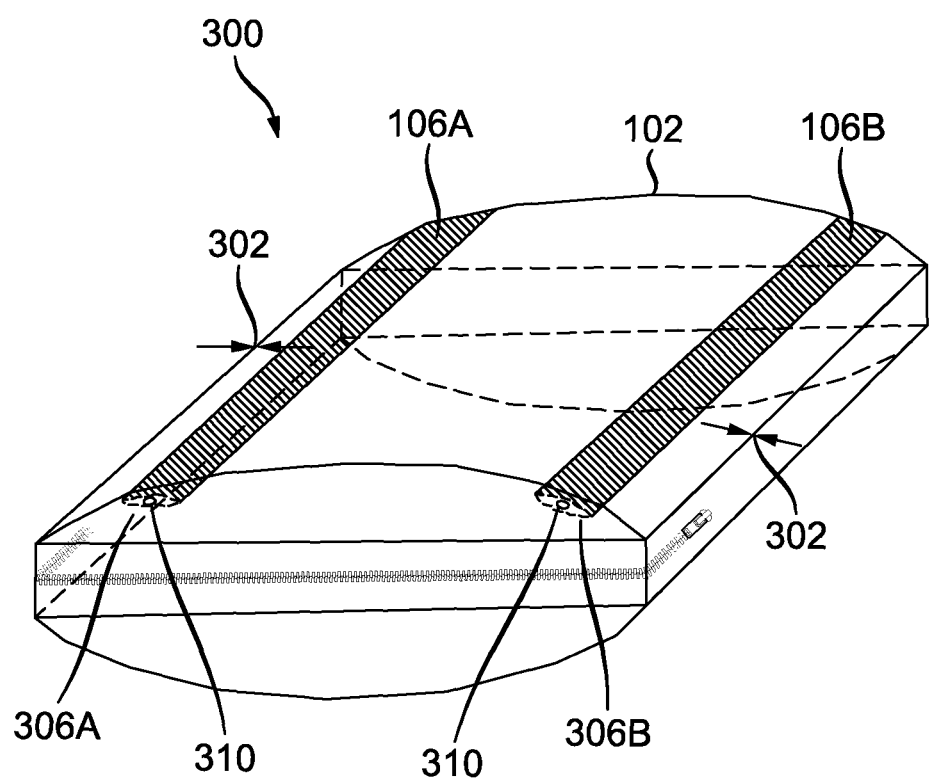
FIG. 3 is a perspective view of a multi-sided aromatic cover in accordance with an embodiment.

FIG. 3 is a perspective view of a multi-sided aromatic cover in accordance with an embodiment. Flexible enclosure 102 may be sized and shaped to partially or fully enclose various bed linens. In one embodiment, flexible enclosure 102 may comprise a multi-sided aromatic cover 300 for receiving and at least partially encasing a pillow. For example, an intersection of at least two sides of flexible enclosure 102 may define an outer edge 302, and one or more aroma-permeable regions, e.g., 106A & B, may be directed along one or more outer edges 302 (e.g., at head, foot and side locations relative to a typical user) such that a user may benefit from a release of aromatic material 310 via one or more cartridges (e.g., 306A & B) regardless of the orientation of aromatic cover 300. Alternatively, one or more aroma-permeable regions may be located along any surface of aromatic cover 300.

Figure 4:
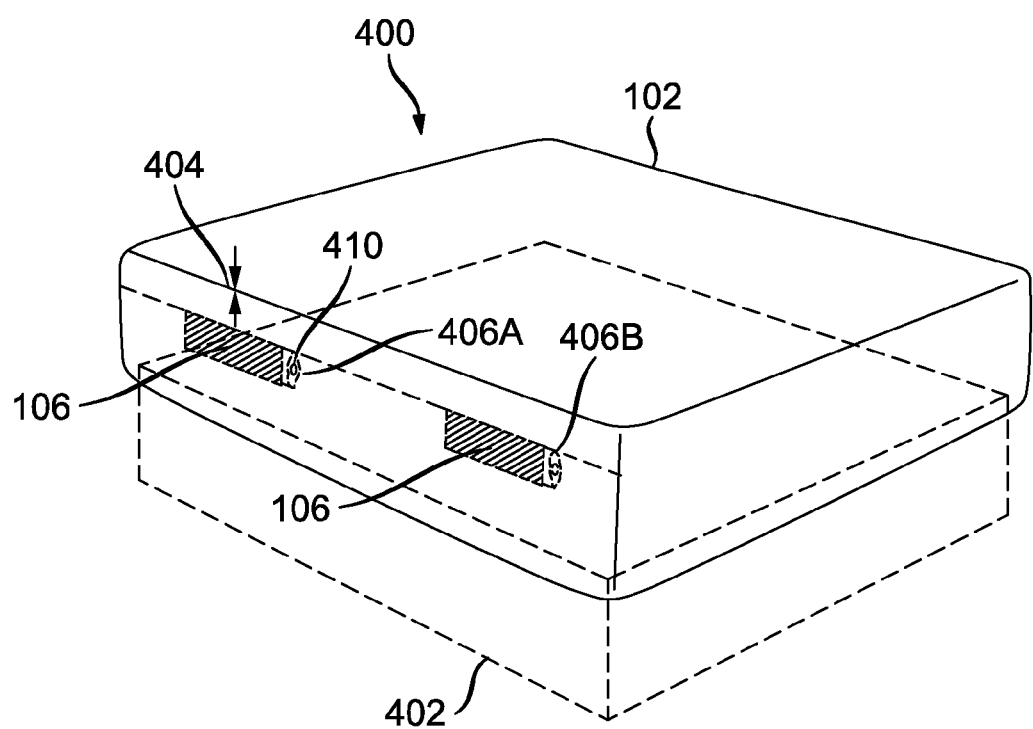
FIG. 4 is a perspective view of a five-sided aromatic mattress cover in accordance with an embodiment.

FIG. 4 is a perspective view of a five-sided mattress cover in accordance with an embodiment. Flexible enclosure 102 may be sized and shaped to enclose the top and skirt (i.e., side) surfaces of a mattress. For example, flexible enclosure 102 may enclose the top and skirt surfaces of a mattress, while leaving an open end 400 at an underside surface such that flexible enclosure 102 may be fitted over the mattress. For example, open end 400 of flexible enclosure 102 may be secured to a mattress via a fastener 402, such as an elastic band-type lining. Alternatively, fastener 402 may be one of a button, zipper, tie string, or hook-and-loop type fastener. In one embodiment, one or more aroma-permeable regions 106 may be directed along one or more outer edges 404 of flexible enclosure 102 to controllably release aromatic material 410 from one or more cartridges 406A & B at a semi-fixed position along inner surface 200.

Figure 5:
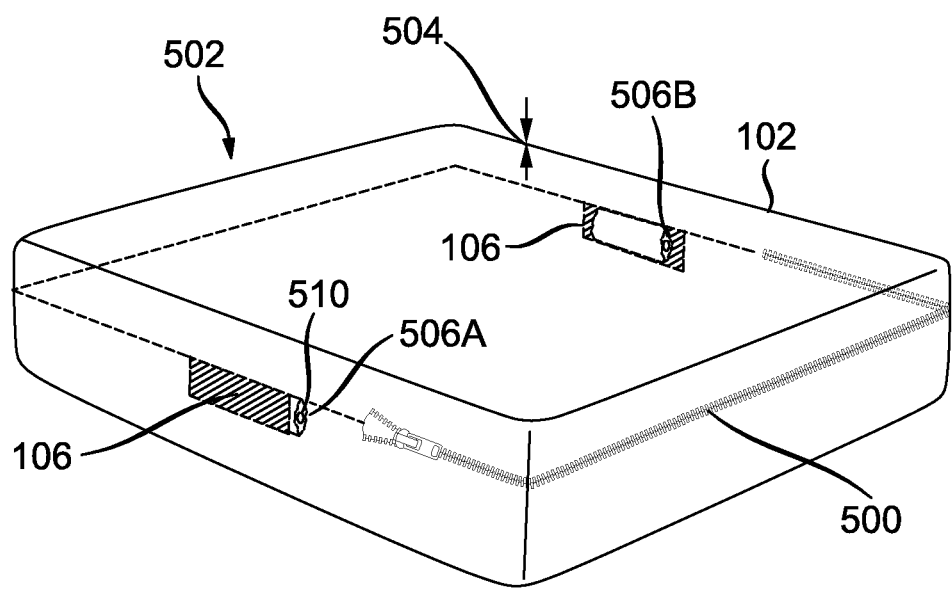
FIG. 5 is a perspective view of a six-sided aromatic mattress cover in accordance with an embodiment.

Alternatively, as shown in the perspective view of FIG. 5, flexible enclosure 102 can be sized and shaped to enclose all six sides of a mattress. For example, flexible enclosure 102 may enclose all six sides of a mattress by including a fastener 500 for closing open end 502. Fastener 500 may be one of a button, zipper, tie string, or hook-and-loop type fastener that allows the flexible cover 102 to encase the mattress and be releasably sealed (e.g., to remove cover 102 from the mattress). In one embodiment, fastener 500 may be configured to prevent dust mites, mold and other allergens from entering flexible enclosure 102. As in FIG. 4 above, one or more aroma-permeable regions 106 may be directed along outer edges 504 of flexible enclosure 102 (e.g., at head and foot locations relative to a typical user) to controllably release aromatic material 510 from one or more cartridges 506A & B at a semi-fixed position along inner surface 200.

Figure 6:
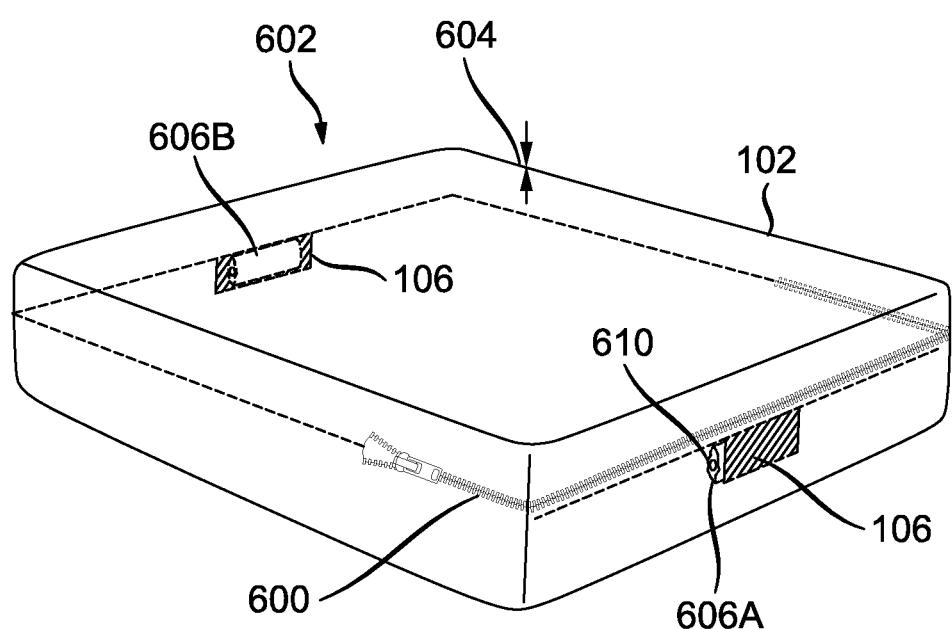
FIG. 6 is a perspective view of another six-sided aromatic mattress cover in accordance with an embodiment.

The perspective view of FIG. 6 illustrates another alternative flexible enclosure 102 that can be sized and shaped to enclose all six sides of a mattress. For example, flexible enclosure 102 may enclose all six sides of a mattress by including a fastener 600 for closing open end 602, and one or more aroma-permeable regions 106 may be directed along outer edges 604 of flexible enclosure 102 (e.g., at side locations relative to a typical user, such as at a location proximate to fastener 600) to controllably release aromatic material 610 from one or more cartridges 606A & B at a semi-fixed position along inner surface 200.

One skilled in the art will recognize that an implementation of an actual aromatic cover may have other structures and may contain other components as well, and that FIGS. 1-6 are a high level representation of some of the components of an aromatic cover for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present disclosure and that various modifications may be implemented by those skilled in the art without departing from the scope and spirit of this disclosure. Those skilled in the art could implement various other feature combinations without departing from the scope and spirit of this disclosure.

We claim:

1. A cover, comprising:
   a flexible enclosure defining an outer surface and an inner surface;
   a cartridge fastener attached to the inner surface, the cartridge fastener configured to releasably retain an aromatic cartridge at a semi-fixed position along the inner surface;
   an aroma-permeable region of the flexible enclosure proximate to the semi-fixed position;
   an aromatic cartridge attached via the cartridge fastener at the semi-fixed location, the aromatic cartridge comprising a quantity of aromatic material, and an aroma-permeable surface enclosing the aromatic material, wherein the aromatic material is controllably released via the aroma-permeable surface; and
   wherein the aroma-permeable region is made of a microfilament material that is different from the material of the remainder of the flexible enclosure.

2. The cover of claim 1, wherein the aromatic material is infused with one of a lavender dry bud, potpourri, rose, sagebrush or chamomile aroma.

3. The cover of claim 1, wherein the aromatic cartridge is substantially equal in size and shape to the aroma-permeable region.

4. The cover of claim 1, wherein the cartridge fastener is one of a button, zipper, tie string, or hook-and-loop fastener.

5. The cover of claim 1, wherein the flexible enclosure further comprises an open end and a closure means for closing the open end.

6. The cover of claim 1, wherein the flexible enclosure is a multi-sided enclosure.

7. The cover of claim 6, wherein an intersection of at least two sides of the flexible enclosure defines an outer edge, and wherein the aroma-permeable region is directed along the outer edge of the flexible enclosure.

8. The cover of claim 6, wherein the flexible enclosure is sized and shaped to at least partially enclose one of a pillow or mattress.

9. The cover of claim 7, wherein the aroma-permeable region is directed at a side location along the outer edge of the flexible enclosure.

10. The cover of claim 1, wherein the material of the flexible enclosure proximate to the aroma-permeable region is a laminated fabric portion.

11. The cover of claim 10, wherein the laminated fabric portion frames one or more edges of the aroma-permeable region.

12. The cover of claim 10, wherein the laminated fabric portion extends along substantially the entire length of the aroma-permeable region.

* * * * *

UNITED STATES PATENT AND TRADEMARK OFFICE
CERTIFICATE OF CORRECTION

PATENT NO. : 8,978,997 B2  
APPLICATION NO. : 13/371917  
DATED : March 17, 2015  
INVENTOR(S) : Jeffrey Bergman and Yao Lujian Page 1 of 1

It is certified that error appears in the above-identified patent and that said Letters Patent is hereby corrected as shown below:

In the claims,

Claim 1,
Column 4, line 60, "location" should be changed to "position".

Signed and Sealed this
Seventeenth Day of November, 2015

Michelle K. Lee
*Director of the United States Patent and Trademark Office*